US008277841B2

(12) United States Patent
Kolawole et al.

(10) Patent No.: US 8,277,841 B2
(45) Date of Patent: Oct. 2, 2012

(54) POLYAMIDE RATE-MODULATED MONOLITHIC DRUG DELIVERY SYSTEM

(75) Inventors: Oluwatoyin Ayotomilola Kolawole, Johannesburg (ZA); Viness Pillay, Sandton (ZA); Yahya Essop Choonara, Lenasia (ZA)

(73) Assignee: University of The Witwatersand, Johannesburg, Johannesburg (ZA)

( * ) Notice: Subject to any disclaimer, the term of this patent is extended or adjusted under 35 U.S.C. 154(b) by 248 days.

(21) Appl. No.: 12/528,175

(22) PCT Filed: Feb. 22, 2008

(86) PCT No.: PCT/IB2008/000395
§ 371 (c)(1),
(2), (4) Date: Nov. 23, 2009

(87) PCT Pub. No.: WO2008/102247
PCT Pub. Date: Aug. 28, 2008

(65) Prior Publication Data
US 2010/0323007 A1 Dec. 23, 2010

(30) Foreign Application Priority Data
Feb. 23, 2007 (ZA) ................................ 2006/09748

(51) Int. Cl.
*A61K 9/22* (2006.01)
(52) U.S. Cl. ........................................................ 424/468
(58) Field of Classification Search .................... None
See application file for complete search history.

(56) References Cited

U.S. PATENT DOCUMENTS

| | | | | |
|---|---|---|---|---|
| 3,765,414 | A | | 10/1973 | Arlen |
| 4,405,360 | A | | 9/1983 | Cardarelli |
| 4,835,248 | A | * | 5/1989 | Bader et al. ................... 528/328 |
| 5,068,220 | A | * | 11/1991 | Vanderbilt et al. ............. 514/5.9 |
| 5,863,991 | A | * | 1/1999 | Warzelhan et al. ........... 525/426 |
| 5,880,220 | A | * | 3/1999 | Warzelhan et al. ........... 525/424 |
| 6,111,058 | A | * | 8/2000 | Warzelhan et al. ........... 528/332 |
| 6,348,499 | B1 | * | 2/2002 | Felgner et al. ................ 514/616 |
| 6,353,084 | B1 | * | 3/2002 | Warzelhan et al. ........... 528/310 |
| 6,565,873 | B1 | * | 5/2003 | Shefer et al. .................. 424/426 |
| 6,790,460 | B2 | * | 9/2004 | Shefer et al. .................. 424/489 |
| 2005/0031577 | A1 | * | 2/2005 | Uhrich ....................... 424/78.27 |
| 2006/0188547 | A1 | * | 8/2006 | S. Bezwada .................. 424/426 |
| 2007/0275027 | A1 | * | 11/2007 | Wen et al. ..................... 424/422 |

OTHER PUBLICATIONS

Oluwatoyin A. Kolawole, Viness Pillay and Yahya E. Choonara. Novel Polyamide 6,10 Variants Synthesized by Modified Interfacial Polymerization for Application as a Rate-Modulated Monolithic Drug Delivery System . Journal of Bioactive and Compatible Polymers May 2007 vol. 22 No. 3 281-313.*
O. Kolawole, V. Pillay, Y. Choonara, M. Danckwerts . Design of a novel polyamide drug carrier for intracranial implantation in the treatment of depression. 2006 AAPS Annual Meeting, Oct. 28-Nov. 2, 2006, W4177.*
Liang-Yin Chu, Yi-Jian Liang, Wen-Mei Chen, Xiao-Jie Ju, Hai-Dong Wang. Preparation of glucose-sensitive microcapsules with a porous membrane and functional gates. Colloids and Surfaces B: Biointerfaces 37 (2004) 9-14.*
S. Alexandridou, C. Kiparissides, J. Fransaer, J.P. Celis. On the synthesis of oil-containing microcapsules and their electrolytic codeposition. Surface and Coatings Technology 71 (1995) 267 276.*
Kenneth Phares et al., "Drug Transport Across Nylon 610 Films. Influence of Synthesis Variables", *Pharmaceutical Research*, 1995, vol. 12, No. 2, pp. 248-256.
P.L. Madan et al., "Nylon Microcapules. II. Effect of Selected Variables on Theophylline Release", *Pharmaceutical Research*, 1989, vol. 6, No. 8, pp. 714-718.
International Search Report and Written Opinion (Application No. PCT/IB2008/000395) Dated Aug. 25, 2009.
International Preliminary Report on Patentability (Application No. PCT/IB2008/000395) Dated Sep. 11, 2009.

* cited by examiner

*Primary Examiner* — Robert A Wax
*Assistant Examiner* — Olga V Tcherkasskaya
(74) *Attorney, Agent, or Firm* — Nixon Peabody LLP

(57) ABSTRACT

This invention relates to a polyamide rate-modulated monolithic drug delivery system comprising at least one active compound and a biodegradable and biocompatible polyamide polymer. The polymer is selected for delivering, in use, the active compound, within a predetermined time frame depending on the biodegradable properties of the polymer, to a target organism or organisms. In one embodiment of the invention the polymer is modified by salting-out or crosslinking the polymeric material to achieve the desired biodegradability characteristics and, consequently, to control the release of the active compound.

26 Claims, 11 Drawing Sheets

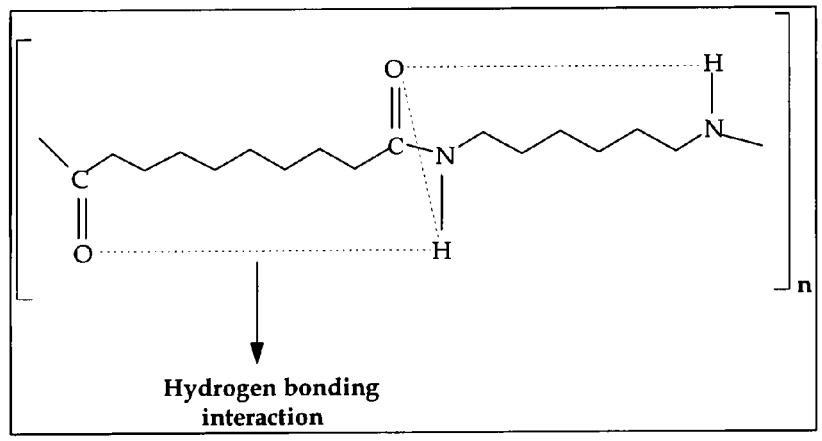
Figure 1: Proposed structural representation of the nature of intramolecular hydrogen bonding within the linear chain of the Polyamide (PA 6,10) crystal.
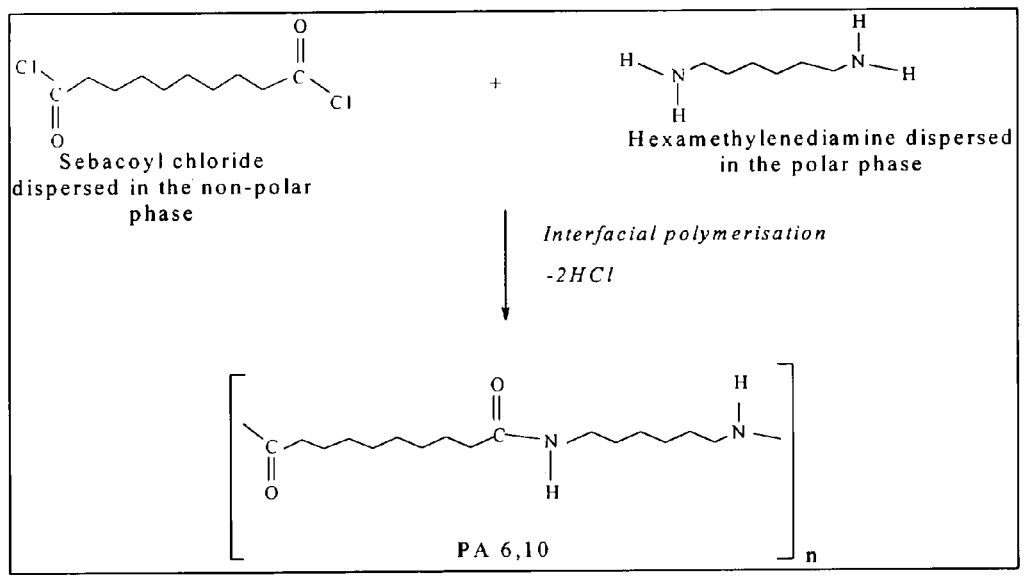
Figure 2: Overall reaction for the synthesis of PA 6,10.

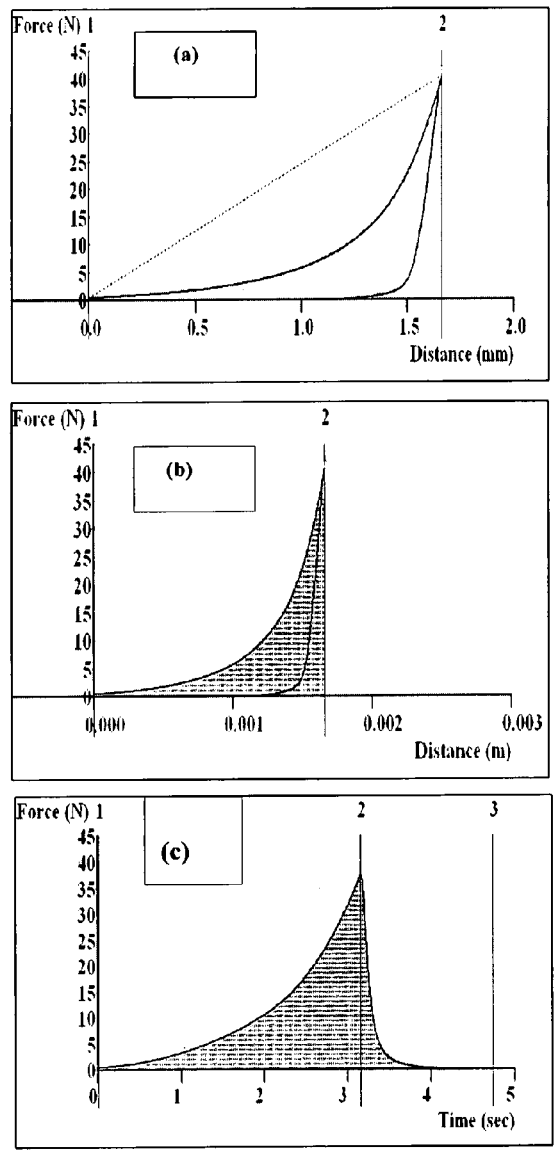
Figure 3: Typical force-distance and force-time profiles of PA 6,10 variants for determining both unhydrated and hydrated (a) matrix hardness, (b) matrix deformation energy, and (c) matrix resilience (unhydrated only) (N=10 in all cases).

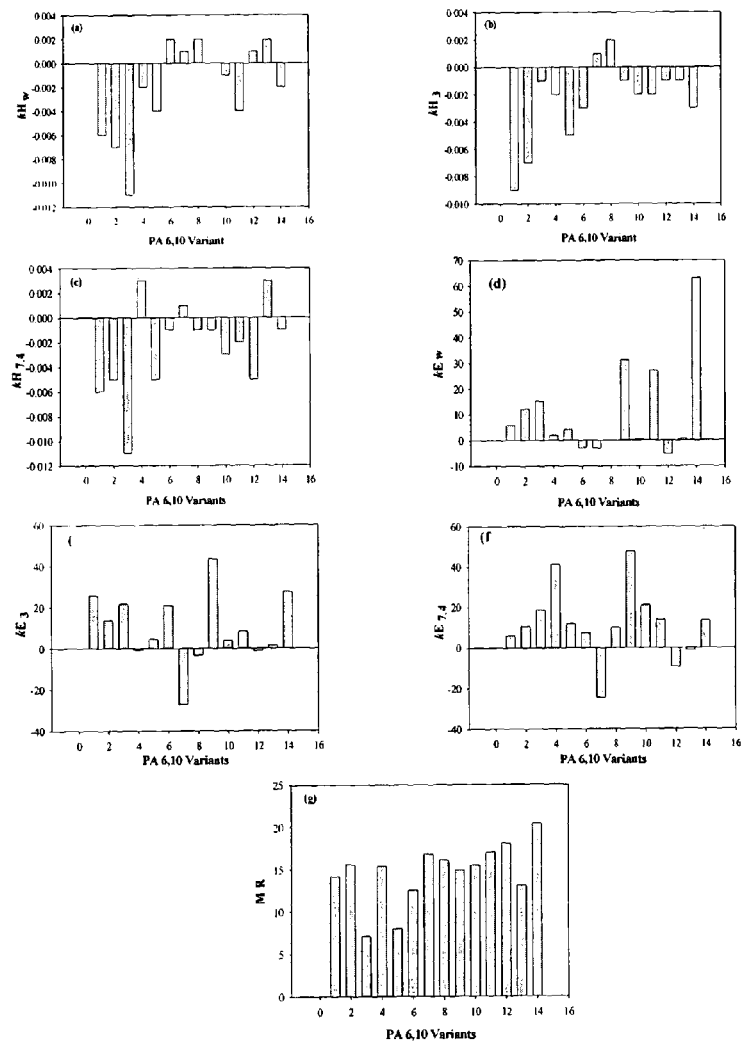
Figure 4: Micromechanical hydrational rate constants and matrix resilience values of the different PA 6,10 variants.

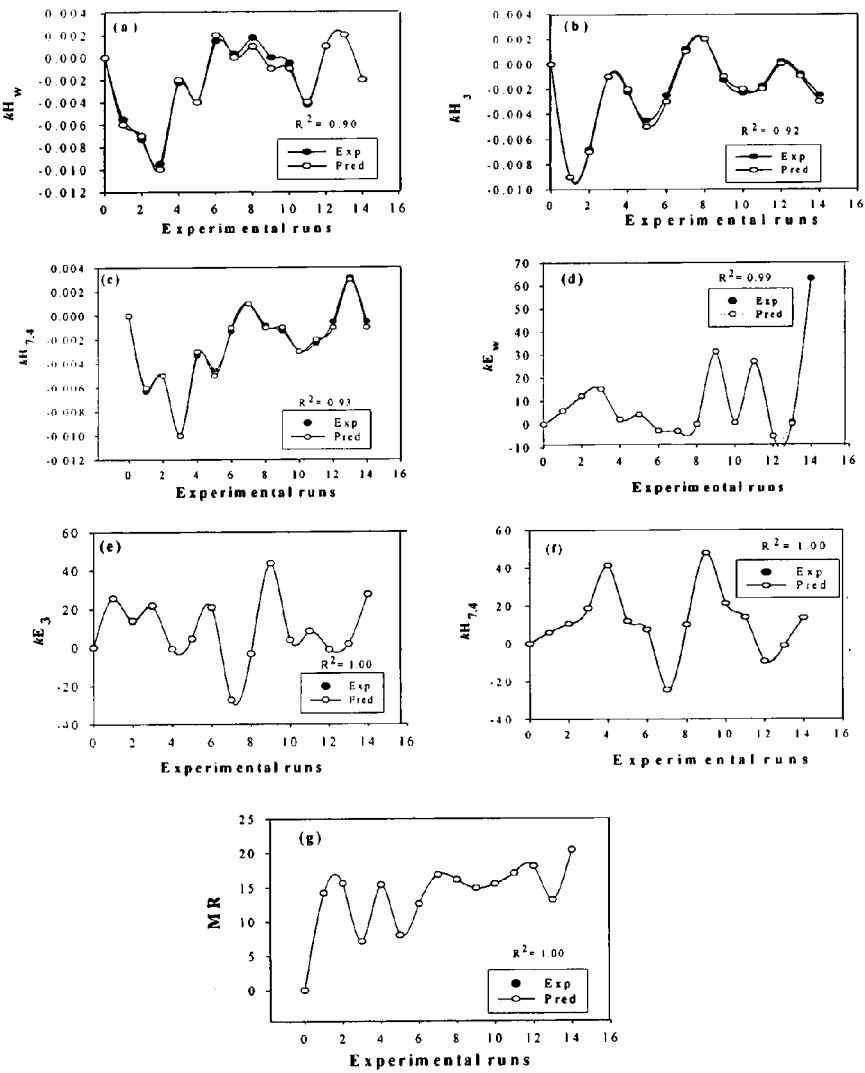
Figure 5: Comparison of experimental and fitted values for the responses (a) $kH_w$, (b) $kH_3$ (c) $kH_{7.4}$, (d) $kE_w$, (e) $kE_3$, (f) $kE_{7.4}$, and (g) MR. Note: $kH_w - kE_{7.4}$ are explained in Table 4 while MR represents the matrix resilience.

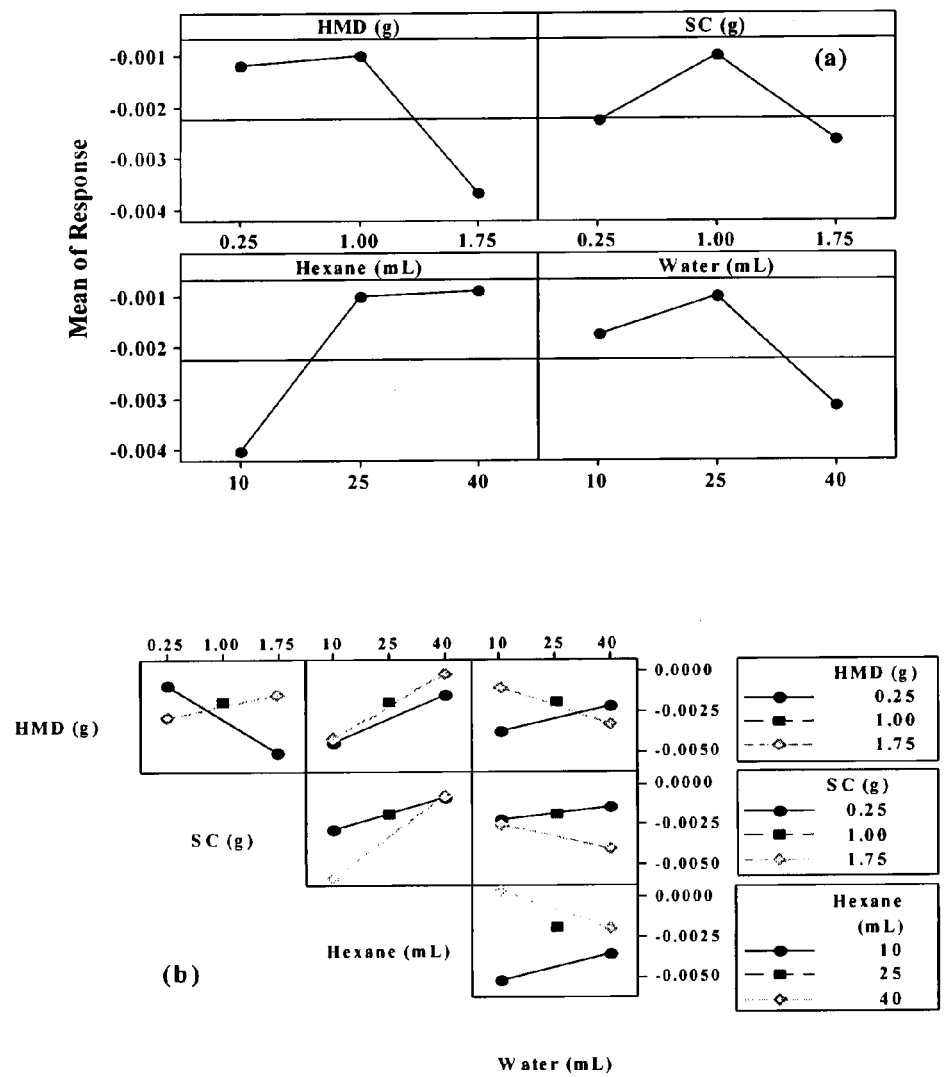
Figure 6: Typical (a) main effects and (b) interaction effects plots of the responses

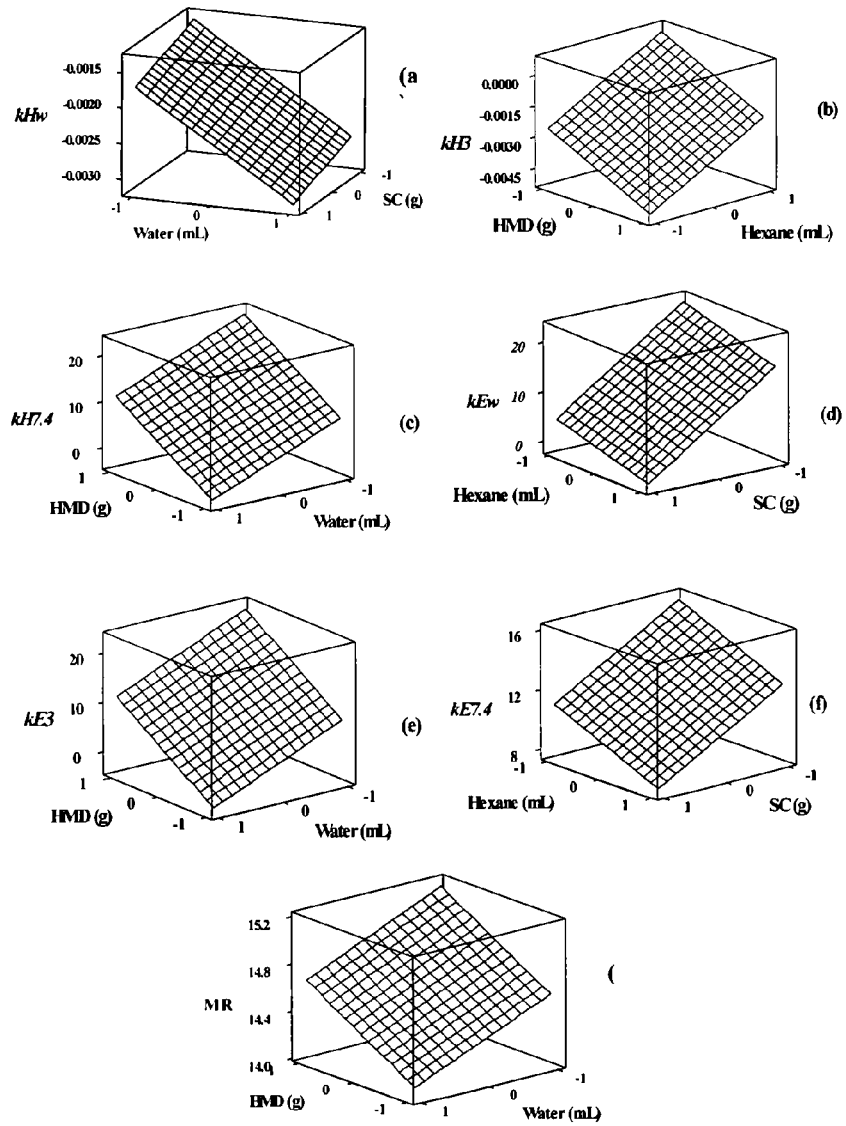
Figure 7: Three-dimensional surface plots for the 7 responses: (a) $kH_w$, (b) $kH_3$ (c) $kH_{7.4}$, (d) $kE_w$, (e) $kE_3$, (f) $kE_{7.4}$, and (g) MR. Note: $kH_w - kE_{7.4}$ are explained in Table 4 while MR represent the matrix resilience.

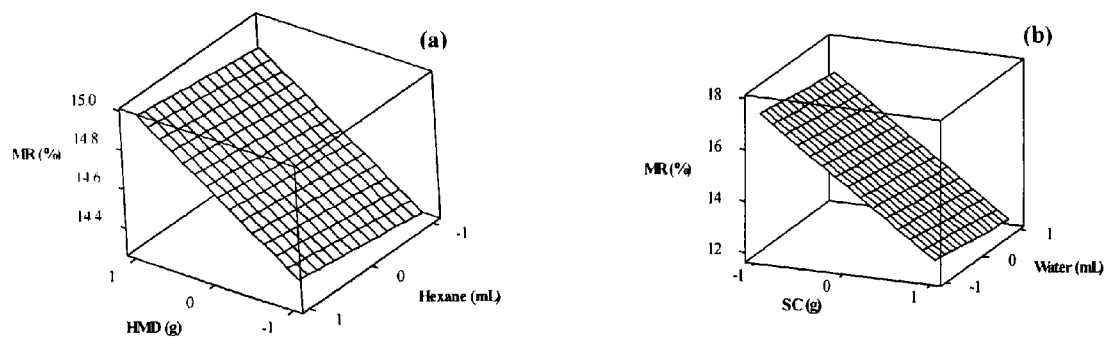
Figure 8: The three-dimensional surface plots showing the effects of the optimized factor levels on the matrix resilience: (a) effect of HMD and hexane (b) effect of SC and deionized water.

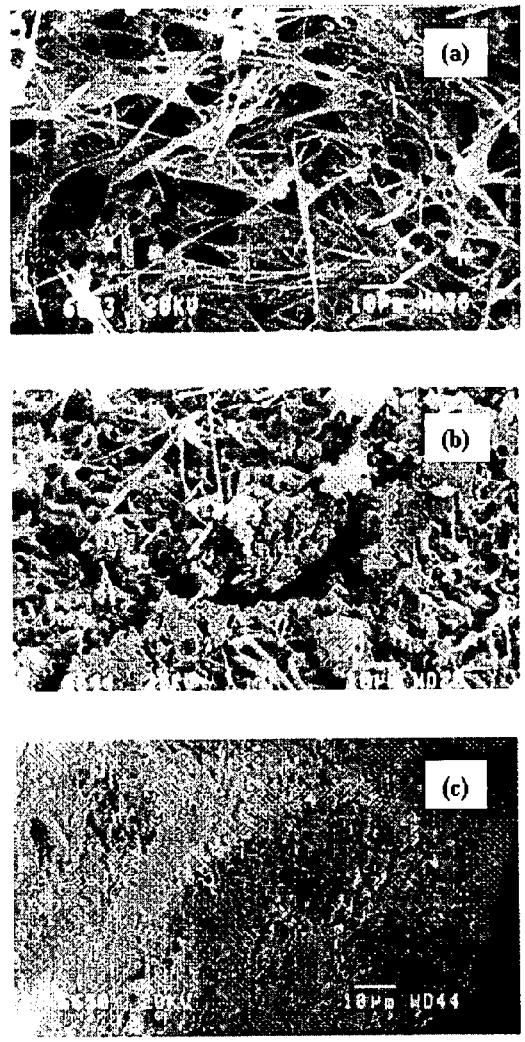
Figure 9: SEM micrographs of the selected PA 6,10 variants with: (a) lowest, (b) highest and (c) optimized matrix resilience showing the morphological diversity as a factor contributing to differences in mechanical properties (magnification ×1000).

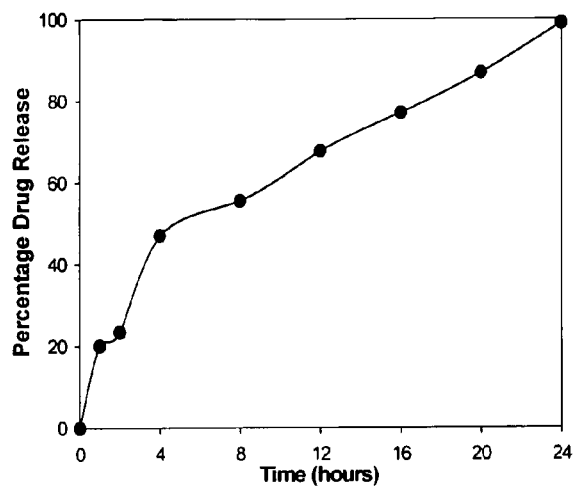
Figure 10: Drug release profile from the standard polyamide 6,10 showing a high initial burst effect.

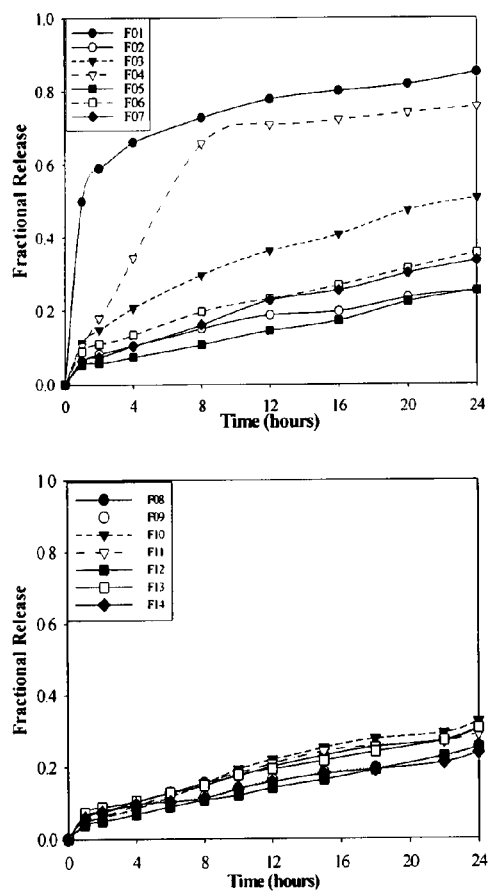
Figure 11: Drug release profiles for the 14 PA 6,10 monolithic matrix formulations in PBS 7.4 as per experimental design template.

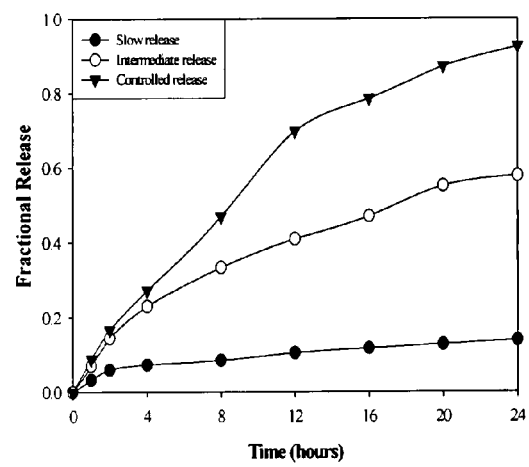
Figure 12: Improved dissolution profiles for the optimized PA 6,10 monolithic matrix formulations showing regulated zero-order and pseudo-zero order drug release with the absence of an initial burst effect and profiles demonstrating drug release for >24 hours.

POLYAMIDE RATE-MODULATED MONOLITHIC DRUG DELIVERY SYSTEM

FIELD OF THE INVENTION

This invention relates to the synthesis and application of polyamides in a monolithic form to optimize the rate and order of drug release.

BACKGROUND TO THE INVENTION

The aliphatic polyamides frequently referred to as nylons form an important group of synthetic polycondensation polymers. They are linear molecules that are semi-crystalline and thermoplastic in nature. They are important and versatile industrial materials because of their superior physical and mechanical properties, namely relatively higher melting points and heat resistance, abrasion resistance, chemical inertness, high modulus, ease of processing, hydrophilicity, superior yield and high level of purity after production [1-8].

These above-mentioned properties of the polyamides stem mainly from their capability to form intramolecular and intermolecular hydrogen bond structures between the amide (—NH—) and carbonyl (—CO—) functional groups, also known as the carbonamide functional moiety, within and between the linear chains in the polyamide crystal respectively [9-12]. A representation of the hydrogen bond interaction between the carbonyl and amide functional groups within the polyamide chain is shown in FIG. 1. The hydrogen bonds are able to retain the molecular chains in an ordered, solid phase before and even after the alkane segments have effectively melted [10]. The length and strength of the hydrogen bond structures are dependent on the polyamide type and the method of synthesis leaving each with slightly different properties [3, 6-11]. The polyamides consist of amide groups separated by alkane segments (FIG. 1) and the number of carbon atoms separating the nitrogen atoms defines the particular nylon type [3, 8, 9]. Cui and co-workers (2004) have successfully subdivided polyamides into six categories namely: even-even, odd-odd, odd-even, even-odd, even and odd [9].

In the present study, the even-even polyamides were selected because of their well-defined structural arrangement due to the fully formed, saturated hydrogen bonds between the molecular chains. This class forms chain-folded sheets and the hydrogen bonds formed between the amide groups in adjacent chains within these sheets provides them with good fiber-forming properties. At room temperature, parallel layers usually form (no inter-sheet hydrogen bonding) that have extended conformations. These sheets can either be stacked together with a progressive shear termed the α-phase or with a staggered shear termed the β-phase giving different triclinic unit cells [7, 11, 12]. Even-even polyamides such as polyamides 6,6; 12,10; 4,8; 4,10; 4,12; 6,10; 6,12; 6,18 and 8,12 have been widely investigated and used in industry [1-21]. Thus far, the investigations concentrated extensively on the characterization of the physicochemical behavior with not much emphasis (when compared with the physicomechanical characteristics) on their performance which is highly responsible for majority of their applications [7, 11-20]. Thus far mechanical assessments conducted on pure polyamides and their blends with other polymeric materials have been in the form of tensile testing, dynamic mechanical analysis and ductility [7, 13, 16, 17].

As far as we know, no study relating the influence of monomeric concentrations and solvent volume ratios to the physicochemical and physicomechanical properties of polyamides using textural profile analysis (TPA) as well as using a modified interfacial polymerization approach to synthesize polyamide variants to develop a rate-modulated monolithic matrix drug delivery system has been reported. Rate-modulated drug delivery technology represents one of the emerging and challenging frontier areas of research in modern medicine and pharmaceuticals [37]. One of the challenging fields of such research is in the fabrication of novel monolithic polymeric systems, using simple process or material modifications such as altering the type of polymer employed during formulation, which has the ability to provide flexible yet rate-modulated drug release performance in a predictable manner achieving more effective therapeutic outcomes and eliminates the risk of both under- and over-dosing.

OBJECT OF THE INVENTION

It is an object of this invention to provide a polyamide rate-modulated monolithic drug delivery system.

SUMMARY OF THE INVENTION

In accordance with this invention there is provided a polyamide rate-modulated monolithic drug delivery system comprising at least one active compound and a biodegradable and biocompatible polyamide polymer having biodegradable and biocompatible properties selected for delivering, in use, the active compound, within a predetermined time frame depending on the biodegradable properties of the polymer, to a target organism or organisms, depending on the biocompatible properties of the polymer.

There is also provided for the active compound to be a pharmaceutical compound for application to humans or animals, alternatively a biocidal composition for use in controlling animal and/or plant pests.

There is further provides for the polymer to be modified by salting-out or crosslinking the polymeric material to achieve the desired biodegradability characteristics and, consequently, to control the release of the active compound.

There is also provided for the polymer and active compound to be formed into a dosage form suitable for oral administration when the active compound is a pharmaceutical composition and, preferably, a tablet.

There is also provided for the polymer and active compound to be formed into a dosage form suitable for implantation in a human or animal body when the active compound is a pharmaceutical composition.

Alternatively there is provided for the polymer and active compound to be formed into a dosage form suitable for application by spraying, alternatively dusting, preferably a flowable powder, when the active compound is a biocidal composition for controlling animal and/or plant pests.

There is further provided for the polymer and the active compound to form a matrix which, in use, biodegrades at a predetermined rate to release the active compound over a predetermined period of time, for a metal hydroxide, preferably sodium hydroxide, alternatively an organic solvent, preferably cyclohexane, to be added to the matrix to, in use, provide added integrity to the matrix and thus influence the rate of outward diffusion thereof when exposed to an aqueous medium to cause a polymeric relaxation reaction to occur in a predictable time dependent manner from the operatively outer boundaries of the matrix towards the operatively inner boundaries thereof and, thus limit outward diffusion of the active compound.

There is also provided for the polyamide polymer to be a synthetic polyamide, preferably a synthetic aliphatic polyamide, for the physicochemical and physicomechanical properties of the polymer to be enhanced so as to control the order and rate of release of an associated active composition in use, and for the synthetic aliphatic polyamide to be a 6,10 variant thereof.

There is also provided for the physicochemical and physicomechanical properties of the polymer to be enhanced, preferably by optimizing one or more of its molecular mass, crystallinity, porosity, melting temperature, solubility, matrix resilience, matrix hardness and deformation energy, by modifying the stoichiometry of a starting monomer composition and/or through the addition of solvent phase modifiers and/or the conditions of polymeric synthesis and delivery system manufacture.

Further, according to another aspect of the invention, there is provided a rate-modulated monolithic drug delivery system comprising synthetic polyamide or a polyamide related polymer, in which is disposed a pharmaceutically active agent.

Preferably, the synthetic polyamide is a synthetic aliphatic polyamide.

Further, there is provided a rate-modulated monolithic drug delivery system comprising synthetic aliphatic polyamide 6,10 variants or a polyamide related polymer, in which is disposed a pharmaceutically active agent.

Preferably, the polymer is one of the synthetic aliphatic polyamide 6,10 variants which is biodegradable and biocompatible.

The polymer may be enhanced by a modified interfacial polymerization approach in order to optimize the release of a pharmaceutical composition in terms of the order and release rate.

The synthetic aliphatic polyamide 6,10 variant or polyamide related polymer is preferably one which has had its physicochemical and physicomechanical properties such as molecular mass, crystallinity, porosity, melting temperature, solubility, matrix resilience, matrix hardness and deformation energy optimized as a result of modifying the stoichiometry of the starting monomer composition and through the addition of solvent phase modifiers and the conditions of polymeric synthesis and delivery system manufacture.

According to a further aspect of the invention, the addition of solvent phase modifiers such as metal hydroxides or organic solvents to the polymer is made to alter the solvent pH and polarity to enhance the matrix integrity of the rate-modulated monolithic drug delivery system, and also influencing the polymeric diffusivity.

Preferably the metal hydroxide is sodium hydroxide and the organic solvent is cyclohexane.

The invention extends to a delivery system for delivering, in use, an active compound within a predetermined time frame using a polyamide rate-modulated monolithic drug delivery system as described above.

BRIEF DESCRIPTION OF AN EMBODIMENT OF THE INVENTION AND OF THE FIGURES

Embodiments of the invention are described below with reference to the accompanying examples and figures in which:

FIG. 1: is a proposed structural representation of the nature of intramolecular hydrogen bonding within the linear chain of the Polyamide (PA 6,10) crystal;

FIG. 2: is an overall reaction for the synthesis of PA 6,10;

FIG. 3: is a typical force-distance and force-time profiles of PA 6,10 variants for determining both unhydrated and hydrated (a) matrix hardness, (b) matrix deformation energy, and (c) matrix resilience (unhydrated only) (N=10 in all cases);

FIG. 4: is a micromechanical hydrational rate constants and matrix resilience values of the different PA 6,10 variants;

FIG. 5: is a comparison of experimental and fitted values for the responses (a) (b) $kH_3$ (c) $kH_{7.4}$, (d) $kE_w$, (e) $kE_3$, $kE_{7.4}$, and (g) MR. Note: $kH_w$-$kE_{7.4}$ are explained in Table 4 while MR represents the matrix resilience;

FIG. 6: is a typical (a) main effects and (b) interaction effects plots of the responses;

FIG. 7: is a three-dimensional surface plots for the 7 responses: (a) $kH_w$, (b) $kH_3$ (c) $kH_{7.4}$, (d) $kE_w$, (e) $kE_3$, $kE_{7.4}$, and (g) MR. Note: $kH_w$-$kE_{7.4}$ are explained in Table 4 while MR represent the matrix resilience;

FIG. 8: is a the three-dimensional surface plots showing the effects of the optimized factor levels on the matrix resilience: (a) effect of HMD and hexane (b) effect of SC and deionized water;

FIG. 9: are SEM micrographs of the selected PA 6,10 variants with: (a) lowest, (b) highest and (c) optimized matrix resilience showing the morphological diversity as a factor contributing to differences in mechanical properties (magnification×1000);

FIG. 10: is a drug release profile from the standard polyamide 6,10 showing a high initial burst effect;

FIG. 11: are drug release profiles for the 14 PA 6,10 monolithic matrix formulations in PBS 7.4 as per experimental design template; and FIG. 12: are improved dissolution profiles for the optimized PA 6,10 monolithic matrix formulations showing regulated zero-order and pseudo-zero order drug release with the absence of an initial burst effect and profiles demonstrating drug release for >24 hours.

DETAILED DESCRIPTION OF AN EMBODIMENT OF THE INVENTION

In order to explore the relationship between the dynamics of the modified synthesis approach and physicochemical and physicomechanical properties of the even-even polyamides, polyamide 6,10 (PA 6,10), also known as polyhexamethylene sebacamide, was used as a model. A modified interfacial polymerization reaction between a diamine and an acid dihalide was employed to form a polymeric film at the interface of two immiscible solvents for the synthesis of PA 6,10 variants. The modification of the interfacial polymerization process was achieved by varying the reaction stoichiometry of the monomers, volume ratios of the solvents and the addition of solvent phase modifiers. The choice of synthesis approach and modifications were based on the established efficiency and simplicity in the synthesis of aliphatic polyamides, which allows for easier process manipulation and reduced production costs as well as the capability of the modification procedure to produce a more physicomechanically robust polyamide structure [7, 10-14, 20].

The physicochemical and physicomechanical behavior of PA 6,10 variants were elucidated from a micro-molecular viewpoint as this offers an in depth and more comprehensive representation of the overall transitions occurring within the structure of the newly synthesized polymer. Three physicomechanical parameters, namely matrix resilience (resistance to deformation), matrix hardness (measure of matrix rigidity) and matrix deformation energy (energy dissipated during matrix rupture) were studied. As part of the characterization process, the subtle effect in pH changes of the hydration media on two of the physicomechanical parameters (i.e. matrix hardness and deformation energy) was also explored.

This study was guided through a statistically robust experimental design approach which was extremely useful for the elucidation, characterization and optimization processes [31-35]. Fourier transform infrared spectroscopy (FTIR) was conducted on the synthesized PA 6,10 variants molecular structures to validate the integrity of their chemical backbone and also to assess the presence of crystalline forms (i.e. α- and β-forms) [11, 12]. Scanning Electron Microscopy (SEM) was utilized to provide information that may be used to correlate the effect of the modified synthesis variables on the physicomechanical behavioural manifestations as it relates to the surface morphologies of the PA 6,10 variants matrices and the ability to control drug release [13, 16]. Furthermore, the in vitro drug release kinetics of a monolithic matrix system employing PA 6,10 variants as the polymeric material was explored. The aforementioned physicomechanical properties as well as the extensive clinical use of the synthetic, aliphatic polyamides as surgical sutures [39, 40, 41] which demonstrates their biocompatibility and non-toxicity make them attractive for use in the design and development of rate-modulated monolithic drug delivery systems.

1. MATERIALS AND METHODS

1.1. Materials

Hexamethylenediamine ($M_w$ 116.2), sebacoyl chloride ($M_w$ 239.1), anhydrous n-hexane, anhydrous potassium bromide, amitriptyline hydrochloride and anhydrous sodium hydroxide pellets were purchased from Sigma Chemical Company (St. Louis, USA). All other reagents used were of analytical grade and used as purchased.

1.2. Constructing the Plackett-Burman Experimental Design Template

A four-factor, three-level, Plackett-Burman design template was constructed for screening the monomer and solvent combinations to synthesize the PA 6,10 variants. The design was appropriate for the intended purpose as it is utilized during preliminary studies to screen and evaluate the important factors that may influence the response(s) under investigation and follows a first-order model [16-18]. The factor levels for the independent formulation variables and the design template are shown in Tables 1 and 2 respectively. The selected dependent variables (or responses) were the physicomechanical parameters namely: (i) unhydrated matrix resilience (%); (ii) unhydrated and hydrated matrix hardness (N/mm$^2$), and (iii) unhydrated and hydrated deformation energy (Joules).

The screening template was compiled using statistical software (Minitab® software, Version 14, Minitab, USA) which required 14 experimental runs including two center points (Table 2). The linear model established which encompassed 5 terms was as follows (Equation 1):

$$\text{Response} = b_0 + b_1[\text{HMD}] + b_2[\text{SC}] + b_3[\text{HXN}] + b_4[\text{DW}] \quad \text{(Equation 1)}$$

where the measured responses (physicomechanical parameters) was associated with each factor level combination, $b_0$ to $b_4$ were the regression coefficients and hexamethylenediamine [HMD], sebacoyl chloride [SC], hexane [HXN] and deionized water [DW] were the independent formulation variables. The lower and upper limits for the independent variables were set based on their ability to undergo optimal polymerization using minimal quantities of chemical reagents.

TABLE 1

Levels of the independent variables employed in the Plackett-Burman Design

| Independent Variables | Factor Levels | | | Units |
|---|---|---|---|---|
| | Low | Middle | High | |
| HMD | 0.25 | 1.00 | 1.75 | g |
| SC | 0.25 | 1.00 | 1.75 | g |
| HEX | 10.00 | 25.00 | 40.00 | mL |
| DW | 10.00 | 25.00 | 40.00 | mL |

1.3. Synthesis of the PA 6,10 Variants Based on the Plackett-Burman Design Template The 14 PA 6,10 variants were synthesized according to the Plackett-Burman design template (Table 2) using combinations of HMD, SC, HXN and DW. A modified interfacial polymerization process was employed for the synthesis of the PA 6,10 variants [14]. The overall chemical reaction is illustrated in FIG. 2. This modification focused on exploring the effect of volume ratio, stoichiometric variations and the addition of solvent phase modifiers such as sodium hydroxide and cyclohexane on the physicochemical and physicomechanical properties of the polyamide 6,10 variants.

For each variant, two solutions were prepared. The first solution comprised specific quantities of HMD dissolved in DW, while the second solution comprised SC in HXN. The concentrations of each solution were based on the combinations outlined in Table 2. The first solution was gradually added to the second to form two immiscible phases which resulted in a polymeric film being formed at the interface. The polymeric film was collected as a mass by rapidly rotating a glass rod at the interface. Upon collection of the polymeric mass, it was thoroughly washed with DW (6×50 mL), lightly rolled on filter paper (diameter 110 mm, pore size 20 μm) to remove any excess solvent and dried to constant weight at 30° C. over 96 hours.

TABLE 2

Plackett-Burman template generated for 4 factors

| Experimental Runs | Quantities of Reactants | | | |
|---|---|---|---|---|
| | HMD (g) | SC (g) | HEX (mL) | DW (mL) |
| 1 | 1.75 | 1.75 | 10.00 | 40.00 |
| 2 | 1.75 | 0.25 | 10.00 | 10.00 |
| 3 | 0.25 | 1.75 | 10.00 | 10.00 |
| 4 | 1.00 | 1.00 | 25.00 | 25.00 |
| 5 | 0.25 | 1.75 | 40.00 | 40.00 |
| 6 | 1.75 | 1.75 | 10.00 | 40.00 |
| 7 | 0.25 | 0.25 | 40.00 | 40.00 |
| 8 | 0.25 | 1.75 | 40.00 | 10.00 |
| 9 | 1.75 | 0.25 | 40.00 | 10.00 |
| 10 | 0.25 | 0.25 | 10.00 | 40.00 |
| 11 | 1.75 | 0.25 | 40.00 | 40.00 |
| 12 | 1.00 | 1.00 | 25.00 | 25.00 |
| 13 | 1.75 | 1.75 | 40.00 | 10.00 |
| 14 | 0.25 | 0.25 | 10.0 | 10.00 |

1.4. Determination of the Physicomechanical Properties of PA 6,10 Variants by Textural Profile Analysis Textural profiling was employed to elucidate the physicomechanical properties of the PA 6,10 variants in terms of their matrix resilience, matrix hardness and deformation energy. Analysis was conducted on both unhydrated and hydrated samples to evaluate the textural transitions associated with the dynamics of differential matrix hydration. A calibrated Texture Analyzer (TA XTplus, Stable Micro Systems, England) fitted with a cylindrical steel probe (50 mm diameter; for matrix resilience) and a flat-tipped steel probe (2 mm diameter; for matrix hardness and deformation energy) was employed. Data was captured at a rate of 200 points per second via Texture Exponent Software (Version 3.2). The parameter settings employed for the analysis are outlined in Table 3. All studies were conducted at room temperature (±21° C.). Samples of 150 mg PA 6,10 variants presented as a square compact of approximately 15 mm×15 mm in dimension was hydrated in 100 mL DW and buffer solutions of pH 3 and 7.4. Samples were removed after 2, 4, 6 and 8 hours of exposure to the hydration media and analyzed for variations in matrix hardness (N/mm$^2$) and deformation energy (J). Matrix resilience (%) was calculated only for the unhydrated samples.

TABLE 3

Textural settings for determining matrix hardness, resilience and deformation energy

| Parameters | Settings |
| --- | --- |
| Pre-test speed | 1 mm/sec |
| Test speed | 0.5 mm/sec |
| Post-test speed | 1 mm/sec |
| Compression force[1] | 40N |
| Trigger type | Auto |
| Trigger force | 0.5N |
| Load cell | 50 kg |
| Compression strain[2] | 50% strain |

[1]Used for matrix hardness and deformation energy
[2]Used for matrix resilience Typical force-distance and force-time profiles generated for computation of the textural parameters are shown in FIG. 3. FIG. 3a indicates a typical force-distance profile for computing the matrix hardness (N/mm$^2$), which is provided by the gradient between the initial force (anchor 1) and the maximum force attained (anchor 2). FIG. 3b depicts the area under the curve (AUC) of a force-distance profile used to calculate the matrix deformation energy (J). FIG. 3c indicates a typical force-time profile used to calculate the matrix resilience (%) which is represented by the percentage of the ratio between the AUC of anchors 2 and 3($AUC_{2,3}$) and anchors 1 and 2 ($AUC_{1,2}$).

1.4.1. Determination of the Physicomechanical Hydrational Rate Constants

In order to elucidate the overall effects of hydration and pH of media on the consistency of the PA 6,10 variants, changes in the matrix hardness and deformation energy with hydration time (2, 4, 6, 8 hours) were evaluated. The intrinsic values obtained at each time point from textural profiling were fitted to a second-order polynomial from which the physicomechanical hydrational rate constants were calculated. This approach provided a concise effect of the hydration process on the physicomechanical integrity of the PA 6,10 variants. A correlation coefficient ($R^2$) value was obtained for all curve-fitting, and was found to range between 0.90 and 1. Table 4 lists the symbolic representations and units for the physicomechanical hydrational rate constants used throughout this study. The computed values for each PA 6,10 variant are shown in FIG. 4.

TABLE 4

Symbolic representations of the micromechanical hydrational rate constants

| Micromechanical Hydrational Rate Constants | Symbolic Representations | Units |
| --- | --- | --- |
| Matrix hardness in deionized water | $kH_w$ | N/mm · hr |
| Matrix hardness in pH 3 | $kH_3$ | N/mm · hr |
| Matrix hardness in pH 7.4 | $kH_{7.4}$ | N/mm · hr |
| Deformation energy in deionized water | $kE_w$ | Joule/hr |
| Deformation energy in pH 3 | $kE_3$ | Joule/hr |
| Deformation energy in pH 7.4 | $kE_{7.4}$ | Joule/hr |

1.5. Determination of the PA 6,10 Variants Percentage Yield

The yield of each variant was calculated as a % w/w with respect to the stoichiometry of each chemical reaction. The relationship employed to calculate the percentage yield was as follows (Equation 2):

$$\text{Percentage Yield (\% w/w)} = \frac{\text{Actual Yield }(g)}{\text{Theoretical Yield }(g)} \times 100 \quad \text{(Equation 2)}$$

1.6. Morphological and Qualitative Characterization of the PA 6,10 Variants

The PA 6,10 variants surface morphology resulting from stoichiometric variation of the monomers was revealed using Scanning Electron Microscopy (SEM) to identify the potential effects of these changes on the geometrical superficial surface, porosity and ultimately the diffusivity of each PA 6,10 variant. Samples (15 mm×15 mm) were sputter-coated with gold-palladium (to minimize the absorbent nature of the polyamides) and viewed under a JSM-840 Scanning Electron Microscope (JEOL 840, Tokyo, Japan) at a voltage of 20 keV and a magnification of 1000×. Several photomicrographs were obtained at various magnifications.

1.7. Determination of Functional Group Vibrational Frequencies by Fourier Transform Infrared Spectroscopy (FTIR)

Infrared spectra were recorded on a Nicolet Impact 400D Fourier Infrared spectrometer (Nicolet Instruments Corporation, Madison, USA) equipped with Omnic Version 3 FTIR software. Powdered samples were used to prepare transparent potassium bromide discs on a Beckman hydraulic press (Beckman Instruments, Inc., Fullerton, USA). Background spectra were collected before running each sample. Samples were analyzed at wavenumbers ranging from 4000 to 400 cm$^{-1}$. All scans were performed in triplicate.

1.8. Statistical Analysis of Data

A one-way ANOVA and three-dimensional surface analysis (Minitab software, V14, Minitab, USA) were performed on the data generated to statistically analyze the effects of variation in the reaction conditions, to compute the precision of the chosen experimental design and to optimize the PA 6,10 variants for their most superior, physicomechanical properties that would confer desirable drug release kinetics. The factor levels of the monomers and solvents represented the independent formulation variables while the physicomechanical parameters represented the dependent variables (i.e. the response parameters).

1.9. Evaluation of the Rate-Modulating Drug Release Ability of PA 6,10 Variants 1.9.1. Construction of the Higher Performance Box-Behnken Design Template A three-factor, three-level Box-Behnken design was built (Minitab Statistical Software, Version 14, Minitab Inc., State College, Pa., USA) for formulation optimization. Fourteen experimental runs with two centre points (Table 9) were generated. The factor levels for the independent formulation variables are listed in Tables 9 and 10 respectively. The selected dependent variables (or responses) were the matrix resilience (MR) and the mean dissolution time at 8 hours ($MDT_8$). This was based on the screening design and combined the modification strategy employed in the synthesis approach of this study namely, variations in stoichiometry and volume ratios of the monomers as well as the addition of solvent phase modifiers.

A non-linear polynomial correlating the relationship between the independent formulation variables and responses was generated (Equation 3) for fitting of the responses.

$$\text{Response} = b_0 + b_1[SC] + b_2[NaOH] + b_3[C\text{-}HXN] + b_4[SC][NaOH] + b_5[NaOH][C\text{-}HXN] + b_6[SC][C\text{-}HXN] + b_7[SC]^2 + b_8[NaOH]^2 + b_9[C\text{-}HXN][C\text{-}HXN]$$

(Equation 3)

Where the fitted responses (i.e. MR and $MDT_8$) was associated with each factor level combination, $b_0 \ldots b_9$ are linear coefficients, [SC], [NaOH] and [C-HXN] are the independent formulation variables.

TABLE 9

Levels of the independent variables employed in the Box-Behnken design

| Independent Variables | Levels | | | Units |
|---|---|---|---|---|
| | Low | Middle | High | |
| SC | 0.25 | 1.00 | 1.75 | g |
| NaOH | 0.25 | 1.00 | 1.75 | G |
| C—HXN | 10.00 | 25.00 | 40.00 | mL |

1.9.2. Synthesis of the PA 6,10 Variants in Accordance with the Higher Performance Box-BEHNKEN Design Template The design template comprised specific quantities of HMD and NaOH dissolved in DW (i.e. polar phase), while the second solution comprised specific quantities of SC evenly dispersed in a mixture of HXN and C-HXN (i.e. non-polar phase). HMD=1.75 g, HXN=40 mL, DW=10 mL were used for all synthesized polyamide 6,10 variants. The simultaneous addition of solvent phase modifiers such as NaOH and C-HXN during synthesis altered the solvent pH and polarity to ultimately enhance the PA 6,10 matrix integrity, diffusivity and subsequently control the rate of drug release from the monolithic drug delivery system. A standard PA 6,10 formulation was also formulated for comparison purposes (Table 11).

TABLE 10

Box-Behnken template for the synthesis of the polyamide 6,10 variants

| Experimental Runs | Quantities of Reactants | | |
|---|---|---|---|
| | SC (g) | NaOH (g) | C—HXN (mL) |
| 1 | 1.750 | 0.000 | 20.000 |
| 2 | 0.250 | 0.875 | 10.000 |
| 3 | 1.000 | 1.750 | 0.000 |
| 4 | 0.250 | 1.750 | 20.000 |
| 5 | 0.250 | 0.000 | 20.000 |
| 6 | 1.750 | 0.875 | 40.000 |
| 7 | 1.000 | 0.875 | 20.000 |
| 8 | 1.000 | 1.750 | 40.000 |
| 9 | 0.250 | 0.875 | 40.000 |
| 10 | 1.750 | 0.875 | 0.000 |
| 11 | 1.750 | 1.750 | 20.000 |
| 12 | 1.000 | 0.875 | 20.000 |
| 13 | 1.000 | 0.000 | 10.000 |
| 14 | 1.000 | 0.250 | 40.000 |

TABLE 11

Composition of Polyamide 6,10 selected as the standard

| HMD (g) | SC (mL) | HEX (mL) | DW (mL) |
|---|---|---|---|
| 2.00 | 3.36 | 40.00 | 40.00 |

Note:
The stoichiometric relationship of this selected standard (reference) of Polyamide 6,10 is 1:1 (i.e. 1 mole of HMD reacted with 1 mole of SC). Also, the volume ratio of the solvents is 1:1 (i.e. 40 mL of Hexane to 40 mL of deionized water)

1.9.3. Preparation of the Monolithic Matrix System Using the Newly Synthesized PA 6,10 Variants Fourteen PA 6,10 variants were formulated into monolithic systems with each matrix comprising a combination of 300 mg of the respective PA 6,10 variants and 50 mg of amitriptyline hydrochloride as the model drug. The powders was blended for 20 minutes using a laboratory-scale blender (CG 100, Kenwood Ltd, UK) and screened through a test sieve of aperture size 1 mm (Endecott's Ltd, London, UK) to ensure reproducibility. Final blends were compressed under a pressure of 1 ton for 60 seconds (at every instance) into flat-surfaced, round compacts each having an average diameter of 13 mm and an average thickness of 4 mm using a Beckman hydraulic press (Beckman Instruments, Inc., Fullerton, U.S.A.).

1.9.4. Determination of Matrix Resilience

The matrix resilience for each monolithic matrix formulation was quantified using a calibrated Texture Analyzer (TA.XTplus, Stable Micro Systems, Surrey, England) fitted with a 36 mm cylindrical steel probe. Matrix resilience was selected for investigation due to its potential impact on the physicomechanical properties, matrix integrity and drug release kinetics of the monolithic matrix system.

1.9.5 In Vitro Drug Release Studies

In vitro drug release studies were performed using a modified USP 25 rotating paddle method in a calibrated six-station dissolution apparatus (Caleva Dissolution Apparatus, model 7ST), agitated at 50 rpm with 500 mL phosphate-buffered saline (PBS) (pH 7.4; 37° C.). The dissolution apparatus included a stainless steel ring mesh contrivance to prevent the hydrated formulation from floating (Pillay and Fassihi, 1998). Samples of 5 mL were withdrawn at specific time intervals over a period of 24 hours and analyzed by ultraviolet spectroscopy (Specord 40, Analytik Jena, AG) at 240 nm (amtryptiline hydrochloride). An equal volume of drug-free PBS was replaced into the dissolution medium to maintain sink conditions. The dissolution data was subjected to a model-independent analysis known as the time-point approach [25, 29]. Briefly, the mean dissolution time set at 8 hours ($MDT_8$) for each formulation was calculated as an average of three readings. The application of the mean dissolution time provided a more precise analysis of the drug release performance and a more accurate comparison of several dissolution data sets [25, 29]. Equation 4 was employed in this regard:

$$MDT = \sum_{i=1}^{n} t_i \frac{M_t}{M_\infty} \quad \text{(Equation 4)}$$

Where $M_t$ is the fraction of dose released in time $t_i=(t_i+t_{i-1})/2$ and $M_\infty$ corresponds to the loading dose.

2. RESULTS AND DISCUSSION

2.1. Synthesis and Yield of the PA 6,10 Variants

The PA 6,10 variants appeared as white, crystalline, compact, sphere-like solids with irregular edges. The yield of each variant was calculated as a percentage w/w and was found to range from 40% w/w to 90% w/w (Table 5). This indicated that apart from the stoichiometry of the reaction which is mainly dependant on the molar ratios of the monomer combinations, the volume ratios and polarity of the solvent systems employed in the synthesis had a significant influence on the PA 6,10 variants properties.

TABLE 5

Percentage Yield of PA 6,10 Variants

| Variants | Yield (% w/w) |
|---|---|
| 1 | 86.00 |
| 2 | 67.50 |
| 3 | 53.55 |
| 4 | 40.11 |
| 5 | 79.87 |
| 6 | 80.70 |
| 7 | 60.00 |
| 8 | 69.00 |
| 9 | 48.25 |
| 10 | 75.00 |
| 11 | 89.00 |
| 12 | 77.00 |
| 13 | 90.54 |
| 14 | 70.11 |

2.2. Elucidation of the Physicomechanical Properties of PA 6,10 Variants

The hydrational rate constants calculated for the matrix hardness and deformation energy, and unhydrated matrix resilience of the 14 experimental formulations are shown in FIG. 4.

2.2.1. Matrix Resilience

This is a measure of the elastic cohesiveness of the PA 6,10 matrices and is defined as the capability of the variant matrices to recover to its original dimensions after deformation caused by an external compressive stress applied by the textural probe during analysis. Generally, a decrease in the concentration of SC and a corresponding increase in HMD coupled with volume ratios of solvents maintained at 1:1 resulted in an increase in matrix resilience (15.1%). In addition, it was observed that at lower quantities of solvents (i.e. 10 mL), still maintaining a solvent volume ratio of 1:1, lower levels of HMD and SC yielded a higher matrix resilience. However, two exceptional cases were noted in which HMD and SC maintained at highest (1.75 g) and lowest (0.25 g) levels respectively with a 4:1 solvent volume ratio HXN:DW and vice versa produced relatively higher values of matrix resilience (i.e. 14.9% and 16.1% respectively) when compared with the highest (i.e. 20.4%).

2.2.2. Physicomechanical Hydrational Rate Constants for the Matrix Hardness and Deformation Energy Matrix hardness is defined as the force required to attain deformation of the PA 6,10 matrices upon application of an external stress. Deformation energy is the energy dissipated in Joules to overcome the adhesive and cohesive forces within the matrices. These parameters which are measures of matrix rigidity or stiffness were employed to view the effects of hydration in media at various pH levels on the integrity of the synthesized PA 6,10 variants. The physicomechanical hydrational rate constants obtained produced both negative and positive values. The negative values describe a decrease in the magnitude of either parameter from the original intrinsic value while the converse applies to the positive values. Due to the hydrophilic nature of the polyamides, the synthesized PA 6,10 variants absorbed the aqueous hydration media which resulted in chain unfolding and subsequent free energy changes within the hydrated structure. Conversely, for few matrices, diffusion of the hydration media resulted in an increase in the magnitude of the matrix hardness and deformation energy indicating that the interaction with DW molecules influenced by variations in pH led to further chain unfolding or entanglement.

With respect to matrix hardness, as pH increased, a decrease and increase in the HMD and SC levels respectively as well as the solvent volume ratio of 4:1 (HXN:DW) produced positive hydrational constant values. This indicated that these combinations hindered matrix disentanglement even on hydration and hence may be more resilient. For the negative values, the reverse chain transitions was observed with volume ratios of either 1:4 or 1:1 (HXN:DW) especially at higher levels. A similar trend was also observed for matrix deformation energy except that lower levels of HMD favored matrix rigidity. Furthermore, volume ratios of 1:1 (maintained at lowest levels) and 4:1 (HXN:DW) generated the highest chain entanglement. The opposite trends were observed for the negative values showing a decrease in matrix strength.

It could be deduced from the observed trends that apart from the monomers which played a major role in determining the physicochemical and physicomechanical integrity of the PA 6,10 matrices, the solvent phase modifiers also contributed to matrix strength with higher levels of HXN increasing polymeric folding (strength) while the converse was true for DW. This is attributable to the hydrophobicity of HXN which is further supported by the addition of C-HXN and the increase in pH afforded by the simultaneous addition of NaOH as a modification strategy during PA 6,10 variant synthesis. Besides, the difference in the ionic composition of each buffer solution affects the diffusivity of the PA 6,10 variants and subsequently the penetration rate of buffer media into the matrix that influences the hydrational response and drug release kinetics of the monolithic drug delivery system.

2.2.3. Proposed Explanation to Observed Trends in Physicomechanical Parameters The observed differences with regard to the physicochemical and physicomechanical properties of each PA 6,10 variant are highly complex. Few explanations linked to the molecular kinetics, the solvent volume ratios, solute contact and the modification strategy of the synthesis approach are as follows:

- The differences in the molar ratio of monomer combinations (stoichiometry of the chemical reaction) which is determined by the concentrations of HMD and SC (the solutes) involved in the synthesis of each PA 6,10 variant.
- The diffusion rate and distance of the monomers (HMD and SC) through the solvents (HXN and DW) to the reaction interface, which is affected by the volume, polarity, pH viscosity and the solute and solvent densities employed in synthesizing each PA 6,10 variant.
- The solute-solute, solvent-solvent and solute-solvent (which vary for different molar combinations) surface characteristics which effect the stress-strain transitions and mobility patterns (dynamic or static) at the reaction interface.
- The magnitude of the contact angle formed between the solute and solvent interface influenced by the level of solute wettability, molar concentration and solvent volume ratios which affects the orientation of the polar and non-polar ionic and covalent micellar molecular ends and forces of molecular interaction.
- Besides the inherent physicochemical characteristics of the solutes and solvents, the differences in their concentrations (molar ratio) and volumes affects the entropy of the reaction system, that also influences the partition coefficient and directly affects the rate and degree of partitioning of solutes into the organic phase where polymerization occurs [14].

2.3. Statistical Analysis of Data 2.3.1. Analysis of Variance

Analysis of variance (one-way) was applied for estimating significance and reliability of the statistical model. The level of confidence accepted for this analysis was 95% where p-values less than 0.05 were considered significant. $R^2$ values of 0.90 and above were considered acceptable due to the complexity of the design. In addition, p-values for the lack-of-fit for all linear regression functions of each response parameter were greater than 0.05, suggesting that the model was accurate, stable and reliable. The Durbin-Watson statistic, d, an index that indicates the freedom of the models from serial correlation, ranged from 1.296-2.400 for all responses, which indicated that the linear regression function was accurate in predicting the responses. The statistical parameters utilized to assess the validity of the model for the respective responses are listed in Table 6.

TABLE 6

Statistical descriptors for the different responses

| Response | $R^2$ | Lack of fit (p-values) | Durbin-Watson d | Significance of terms (p-values) | | | |
|---|---|---|---|---|---|---|---|
| | | | | HMD[1] | SC[2] | HEX[3] | DW[4] |
| $kH_w$ | 0.82 | 0.57 | 1.85 | 0.03 | 0.03 | 0.04 | 0.03 |
| $kH_3$ | 0.79 | 0.85 | 1.90 | 0.02 | 0.02 | 0.04 | 0.03 |
| $kH_{7.4}$ | 0.88 | 0.49 | 1.30 | 0.03 | 0.01 | 0.02 | 0.03 |
| $kE_w$ | 0.99 | 0.08 | 2.35 | 0.01 | 0.04 | 0.01 | 0.02 |

TABLE 6-continued

Statistical descriptors for the different responses

| Response | $R^2$ | Lack of fit (p-values) | Durbin-Watson d | Significance of terms (p-values) | | | |
|---|---|---|---|---|---|---|---|
| | | | | HMD[1] | SC[2] | HEX[3] | DW[4] |
| $kE_3$ | 1.00 | 0.18 | 2.40 | 0.04 | 0.03 | 0.02 | 0.04 |
| $kE_{7.4}$ | 0.70 | 0.77 | 1.32 | 0.04 | 0.04 | 0.04 | 0.04 |

[1]Hexamethylenediamine
[2]Sebacoyl Chloride
[3]Hexane
[4]Deionized water

All factors were statistically significant ($p<0.05$) showing that the independent formulation variables (i.e. the different levels of monomers and solvents) had a major influence on the physicomechanical parameters of the PA 6,10 variants. In other words, this outcome suggested that the different factor levels (i.e. the chemical reaction stoichiometry or the molar concentration ratio of the combination of monomers and volume ratios of the solvents) played a major role in determining the matrix integrity i.e. the degree of chain folding or unfolding during the process of hydration.

2.3.2. Comparison of the Experimental and Fitted Response Values

A diagnostic procedure was employed to fit the values of the response parameters in order to evaluate the reliability of the model. A high degree of correlation between the fitted and experimental values based on the ANOVA for each response was evident that further revealed the accuracy of the statistical design. This is illustrated for all the responses in FIG. 5.

2.3.3. The Main and Interaction Effects on the Responses

The main effects plots were employed to visually represent the influence of the independent formulation variables on the responses and compare the relative strength of the effects at different factor levels (FIG. 6a). It was observed that the mid-limit value for each factor (HMD 1 g, SC 1 g, DW 25 mL, HXN 25 mL) produced a central point for changes (increase or a decrease) in the mean of all responses. FIG. 6a, demonstrates the synergistic effects of the independent formulation variables (SC, HMD, HXN and DW) on the response up to the mid-limit from where an increase in a factor level resulted in a decrease in the measured response with the reverse observed for HXN. The interaction plots are used to visualize the mathematical interaction effects of the factors on the physicomechanical responses. FIG. 6b illustrates the existence of interactions between the independent variables which could either lead to a decrease or increase in the magnitude of the measured responses. In other words, it can be stated that the effects of the different factor levels on the responses are not solely dependent on the individual monomer or solvent but also on their synergistic or antagonistic interactions.

2.4. Constrained Optimization of the PA 6,10 Variants Physicomechanical Properties In addition to elucidating the linear regression equations relating the dependent to independent formulation variables, PA 6,10 variants was optimized in terms of its matrix resilience, due to its significant influence on the overall matrix integrity and strength. The magnitudes of the matrix hardness and deformation energy, which are measures of the level of matrix rigidity, are also relatively dependent on the resilient nature of the PA 6,10 matrix [25]. In this study the optimal experimental parameters were computed using the generalized reduced gradient linear optimization algorithm. Constraints (independent variables) were based on the limits in Table 1 in an effort to obtain an optimized PA 6,10 variant with a matrix resilience (%) greater than or close to the realistically attainable value of 20%. The optimized levels of the factors (HMD, SC, HXN, DW) that achieved the desired matrix resilience are depicted in Table 7. The experimental (23.02%) and predicted (17.65%) values were relatively close to the desired value of 20%.

TABLE 7

Optimized resilience obtained by constraints applied to response factors

| Optimized levels of factors | | | | Response % | | |
|---|---|---|---|---|---|---|
| HMD | SC | HEX | DW | | | |
| (g) | (g) | (mL) | (mL) | Des[1] | Pre | Exp[3] |
| 1.75 | 0.25 | 40 | 10 | 20.0 | 17.65 | 23.02 |

[1]Des = Desired value
[2]Pred = Predicted value
[3]Exp = Experimental value 2.4.1. Surface Plots to Explain the Significant Effects of the Factors on the Matrix Resilience Presenting the optimized experimental results in the form of three-dimensional surface plots, FIG. 8a indicates that higher levels of HXN and HMD increased matrix resilience. Conversely, FIG. 8b depicted that higher values of matrix resilience were attained with decreasing concentrations of SC and DW.

A proposed chemical explanation to this mathematical interpretation is that an increase in the level of HMD and HXN significantly increased the potential of the PA 6,10 matrix to form a stronger and more compact network (the crystalline lamellar structure) due to the hydrophobicity of HXN, the hygroscopic nature of HMD and furthermore enhanced by the hydrophobic nature of SC. A high volume of HXN protects the ionic moiety ($Cl^-$) in from hydrolysis to sebacic and hydrochloric acid which may reduce the rigidity of the polymeric backbone. Maintaining SC at the lowest level stabilizes its contact with the polar phase. The complementary effects of HMD and SC maintain the optimal level of polymeric hydration, enhancing molecular packing. As much as DW has the capacity to decrease matrix resilience, minimum levels are required in retaining an optimal level of matrix flexibility by maintaining the inter-chain hydrogen bond interactions, which suppresses the shear slip of the polymeric chains during deformation thus increasing the elasticity of the PA 6,10 variants [10].

2.5. FTIR Spectrophotomeric Analysis

FTIR studies were conducted on the 14 PA 6,10 variants to assess the integrity of the structural backbone and identify salient functional groups. The major functional group absorption bands are consistent with the anticipated chemical composition (i.e. all showed characteristic methylene and amide absorption bands) (Table 8). The successful integration of variations in physicomechanical properties of the 14 PA 6,10 variants' polymeric backbones is also substantiated by the subtle differences in vibrational frequency values of the salient functional groups attained by FTIR studies.

TABLE 8

Vibrational frequencies of the PA 6,10 variants

| [1]Exp Runs | C—H stretch | C—O | C=O | N—H | C—N | $CH_2$ wag | $CH_2$ rock |
|---|---|---|---|---|---|---|---|
| 1 | 2933.66 | 1239.82 | 1707.72 | 3301.61 | 1189.82 | 1466.08 | 724.63 |
| 2 | 2927.24 | 1245.20 | 1708.81 | 3309.06 | 1331.46 | 1470.93 | 726.33 |
| 3 | 2919.03 | 1240.59 | 1607.80 | 3306.09 | 1301.88 | 1466.01 | 724.75 |
| 4 | 2932.58 | 1243.01 | 1701.31 | 3303.91 | 1302.21 | 1450.03 | 737.18 |
| 5 | 2933.64 | 1240.74 | 1702.27 | 3303.53 | 1301.90 | 1467.63 | 724.85 |
| 6 | 2932.92 | 1241.70 | 1697.36 | 3306.46 | 1302.04 | 1466.32 | 736.52 |
| 7 | 2962.78 | 1244.76 | 1720.01 | 3308.72 | 1308.58 | 1466.67 | 723.24 |
| 8 | 2931.93 | 1242.08 | 1702.25 | 3304.67 | 1302.27 | 1480.90 | 679.02 |
| 9 | 2937.60 | 1283.62 | 1701.88 | 3302.34 | 1319.97 | 1453.50 | 732.53 |
| 10 | 2930.89 | 1210.35 | 1705.78 | 3307.91 | 1323.63 | 1451.55 | 700.08 |
| 11 | 2928.01 | 1246.26 | 1736.21 | 3305.81 | 1321.13 | 1474.35 | 731.97 |
| 12 | 2928.09 | 1243.27 | 1698.39 | 3302.91 | 1343.05 | 1431.03 | 736.50 |
| 13 | 2927.50 | 1245.21 | 1687.31 | 3304.86 | 1331.85 | 1477.15 | 735.71 |
| 14 | 2928.62 | 1243.63 | 1695.77 | 3306.51 | 1326.29 | 1448.87 | 735.88 |
| Opt* | 2970.81 | 1249.75 | 1705.11 | 3309.01 | 1289.77 | 1469.66 | 742.85 |

Opt* - the optimized PA 6,10;

Unit of measurements = $cm^{-1}$;

[1]Experimental

The subtle differences observed in the vibrational frequencies may be due to changes in the stoichiometry and the solvent volume ratio interacting with the physicochemical and physicomechanical properties exhibited by the synthesized PA 6,10 variants. This may also be attributed to the varying effects of the aforementioned changes in the strength and length of the intramolecular hydrogen bond structures within the linear chains of the polyamides (FIG. 1). This affects the electron cloud around the sigma ($\sigma$) single complex (saturated bonds) of methylene (—$CH_2$—) and amide (—NH—) groups along the chain which subsequently affects the mobility of the pie ($\pi$) electrons (unsaturated bonds) of the carbonyl functional group (C=O). These structural alterations influence the vibrational frequencies, absorption bands and the peak intensities which may produce changes in the physicochemical and physicomechanical properties of the PA 6,10 variants synthesized (Table 8). Moreover, the effects of the abovementioned factors are also reflected in the slight differences in the pattern of the characteristic finger print region (1300-909 $cm^{-1}$). Absorption bands within the conformationally sensitive region of 750-500 $cm^{-1}$ were observed for the synthesized matrices [11]. This suggests the presence of the conformational crystalline forms namely the $\alpha$- and/or $\beta$-phase described for the even-even polyamides at room temperature and may affect the PA 6,10 variants crystal lattice which directly or indirectly influences the physicomechanical behavior of the polymer and drug release kinetics when formulated as a monolithic drug delivery system.

2.6. Surface Morphology of the PA 6,10 Variants

Three samples were selected to explore the influence of variations in the factor levels on the surface morphology of the respective PA 6,10 variants. Sample selection was based on the pre-optimized lowest resilience (i.e. 7.1%, Sample 3), highest resilience (i.e. 20.4%, Sample 14) and the mathematically optimized system to show variations in the morphological structure (FIG. 9).

Analysis indicated that the difference in combinations of the factor levels employed in the synthesis of the PA 6,10 variants influenced the surface morphology of the selected matrices and that this physical transformation played a critical role in establishing their physicomechanical characteristics. The surface morphologies varied from being: (i) highly porous, web-like (showing low resilience) (FIG. 9a), (ii) closer packed which appear to be more clustered (showing high resilience) (FIG. 9b), and (iii) to a smooth, continuous and firm surface of the optimized system with balanced matrix resilience (FIG. 9c). The PA 6,10 variant surfaces were dissimilar in surface geometry and porosity. Significant changes in porosity may directly impact the matrix diffusivity with subsequent profound favorable effects on the ability of PA 6,10 to control drug release.

A proposed explanation for this is the effect of the polyamide linear chain surface geometry on the packing efficiency of the entire PA 6,10 variant structure producing a direct influence on the combined lamellar crystalline structure of polyamide (a function of chain folding and shear slip of the hydrogen bonded sheets). The conspicuous differences revealed in the photomicrographs demonstrated the pinpointing effect of the stoichiometry of the chemical reaction on the surface morphology and consequently the physicomechanical behavior of the PA 6,10 variants.

2.7. Fourier Transform Infra Red Spectroscopy (FTIR)

Specific transmitting bands of amide (N—H, 3306.44-3401 $cm^{-1}$), methylene segments (C—H stretch, 2850-2900 $cm^{-1}$), $CH_2$ wag (1442-1466.15 $cm^{-1}$) and rock (700-750 $cm^{-1}$) movements, carbonyl groups (C=O, 1690-1740 $cm^{-1}$), C—N—C scissors vibrations (480-510 $cm^{-1}$) of the 14 PA 6,10 variants correlated with the referenced chemical structures. In addition, the range of vibrational frequency values obtained for the PA 6,10 variants analysis was closely related to the ranges generated for variants synthesized by the Plackett-Burman design (Table 8). This revealed consistency in the basic backbone structure of all variants irrespective of the modification strategy applied during synthesis to improve the purity and matrix integrity of the PA 6,10 variants.

2.8. In Vitro Drug Release Studies

Diverse release patterns were observed for the 14 PA 6,10 monolithic formulations which may be associated with the varying degrees of polymerization. The $MDT_8$ values for each dissolution profile using Equation 4 were calculated from the dissolution profiles generated. It was observed that formulations with a low $MDT_8$ value exhibited steady drug release while the converse was true for formulations with high $MDT_8$ values. $MDT_8$ values for all 14 PA 6,10 monolithic formulations ranged between 2.1 and 11.7.

Compared to the optimized monolithic matrices a level burst release of drug (20.11%) was observed for the selected standard PA 6,10 (FIG. 10). Drug release at $t_{24\ hours}$ was 99%. Evidence of a lower level of mechanical strength and controlled drug release properties when compared to the optimized formulation synthesized by modified interfacial polymerization (FIG. 12).

2.9. Constrained Optimization of the PA 6,10 Monolithic Matrix System

A constrained optimization technique was employed to optimize the PA 6,10 monolithic matrix system with regard to achieving different rates and order of drug release profiles ranging from first-steady/intermediate- to ideal zero-order release kinetics. The experimental results obtained were fitted within set constraints for predicting the optimal formulations using a Response Surface Optimizer (Minitab V14, USA). Constraints were set to obtain levels of independent formulation variables that would simultaneously maximize or minimize matrix resilience and the $MDT_8$ with respect to the desired release profiles. The matrix resilience and $MDT_8$ were targeted at different levels (Table 11) providing the desirability function was equal to one which indicated the accuracy and efficiency of the model. Based on the set constraints the optimal factor levels that achieved the desired numerical values of the significant response parameters are listed in Table 13.

TABLE 12

Numerical targets set for the significant response parameters to generate the desired drug release performances

| Set Targets for the Response Parameters | | Desired Drug Release Patterns |
|---|---|---|
| Matrix Resilience (%) | $MDT_8$ | |
| 65.00 | 1.10 | Steady |
| 45.85 | 4.27 | Intermediate |
| 43.19 | 7.02 | Zero-order |

TABLE 13

Levels of significance for the response parameters

| Response Parameters | p-values | $R^2$ | Lack of fit |
|---|---|---|---|
| MR[a] | 0.031 | 0.907 | 0.324 |
| $MDT_8$[b] | 0.013 | 0.948 | 0.264 |

[a] Matrix resilience,
[b] Mean dissolution time

TABLE 14

Experimental and predicted response values performed at optimal factor levels

| Desired Drug Release Patterns | Selected Factor Levels | | | Response | | | |
|---|---|---|---|---|---|---|---|
| | | | | MR[a] | | MDT[b] | |
| | SC (g)[c] | NaOH (mL)[d] | C-HXN (mL)[e] | Pred[f] | Exp[g] | Pred[f] | Exp[g] |
| Slow | 0.63 | 0.10 | 40.00 | 64.00 | 65.20 | 1.25 | 1.17 |
| Intermediate | 1.49 | 0.10 | 2.92 | 44.00 | 45.33 | 4.50 | 5.00 |
| Controlled | 0.20 | 0.40 | 10.00 | 42.00 | 41.55 | 6.92 | 7.00 |

[a] Matrix resilience,
[b] Mean dissolution time,
[c] Sebacoyl chloride,
[d] Sodium hydroxide,
[e] Cyclohexane,
[f] Predicted values,
[g] Experimental values A close relationship between the experimental and predicted values was observed ($R^2 > 0.90$). This outcome demonstrated the stability and validity of the optimization procedure. The monolithic matrix system was then prepared using the optimized PA 6,10 variants synthesized from the model-predicted optimal factor levels. Representative dissolution profiles of the optimized formulations are shown in FIG. 12.

3. CONCLUSION

The Plackett-Burman design was employed for the synthesis of 14 aliphatic PA 6,10 variants by a modified interfacial polymerization process. The design revealed variations in the physicochemical and physicomechanical properties of the PA 6,10 variants due to the variation in factor levels employed during synthesis. These were measured in terms of the PA 6,10 variants matrix resilience, matrix hardness and deformation energy. This finding served as a useful means in providing some explanation to the transformational processes occurring from a physicomechanical viewpoint. ANOVA and response surface plots indicated that the factor levels had a significant influence ($p < 0.05$) on the measured physicomechanical parameters. As part of the elucidative process, based on the information provided, PA 6,10 variants were optimized for their physicomechanical properties. The matrix resilience was selected for optimization due to its significant impact on matrix integrity and drug release kinetics. In addition, the experimental and fitted values were closely correlated indicating the statistical design to be an accurate and reliable tool. Furthermore, SEM substantiated the diversity observed for the physicomechanical properties and revealed that the surface morphological character of the PA 6,10 variants are a function of their micro-particulate morphology, chain folding and crystal packing with the chemical structural backbone unchanged for all variants.

Furthermore, this study also verifies the utility, reliability and efficiency of Design of Experiments (DOE) over the existing One Variant At a Time (OVAT) technique. It has enabled us to provide some explanation about the physicomechanical transitional states that may possibly occur in PA 6,10 variants synthesized using the modified interfacial polymerization approach described. Furthermore, the possibility of employing PA 6,10 variants in the development of a novel polymeric rate-modulated monolithic matrix drug delivery system was found to be suitable using amitriptyline as the model drug. The more statistically robust Box-Behnken design provided an optimized PA 6,10 variant which was formulated into a monolithic matrix system that displayed diversified rate-modulating drug release ranging from steady to ideal zero-order release. The outcome of this work provides insight to a better comprehension of the properties of PA 6,10 variants and their ability to control drug release and be utilized as an polymeric material to achieve rate-modulated drug delivery of improved monolithic form.

4. REFERENCES

1. Huang, Y., Li, W. and Yan, D. (2003). Crystalline transition of nylons 12, 20 and 10,20. *European Polymer Journal*, 39, 113-1140.
2. Li, Y., Yan, D. and Zhu, X. (2001). Crystal forms of nylon 10, 12 crystallized from melt and after solution casting. *European Polymer Journal*, 37, 1849-1853.
3. Cui, X. and Yan, D. (2005). Preparation, characterization and crystalline transitions of odd-even polyamides 11, 12 and 11,10. *European Polymer Journal*, 41, 863-870.
4. Murthy, N. S. (1999). Interactions between Crystalline and Amorphous Domains in Semicrystalline Polymers: Small-Angle X-ray Scattering Studies of the Brill Transition in Nylon 6,6. *Macromolecules*, 32, 5594.
5. Sikorski, P., Jones, N. A, Atkins, E. D. T. and Hill, M. J. (2001). Measurement of the intersheet shear along the chain axis in nylon6. *Macromolecules*, 34, 1673.
6. Hopf G. (2001). A Publication of nylon 12—Huels in comparison to other nylons, chemische werke huels AG, West Germany, pages 1-22.
7. Konishi, R. and Ito, M. (2004). Relation between ductility and segmental mobility on nylon 6. *Polymer*, 45, 5191-5198.
8. Hedge, R. R., Dahiya, A. and Kamath, M. G. (2004). Nylon fibers, pages 1-11 (http://web.utk.edu/~mse/pages/textiles/nylon%20fibers.htm).
9. Cui X., Liu Z. and Yan D. (2004). Synthesis and characterization of novel even-odd nylons based on undecanoic acid. *European Polymer Journal*, 40, 1111-1118.

10. Jones, N. A., Atkins, E. D. T., Hill, M. J., Cooper, S. J. and Franco, L. (1997). Chain-folded lamellar crystals of aliphatic polyamides. Investigation of nylons 4 8, 4 10, 4 12, 6 10, 6 12, 6 18, and 8 12. *Polymer,* 38: 2689-2699.

11. Franco, L., Navarro, E., Subirana, J. A. and Puiggali, J. (1998). Incorporation of glycine in even-even polyamides. Part II: Nylons 6, 10 and 12, 10. *Polymer;* 40, 2429-2438.

12. Franco, L., Navarro, E., Subirana, J. A. and Puiggali, J. (1998). Incorporation of glycine in even-even nylons disrupts their characteristics all-trans conformation. *Polymer,* 39: 5553-5560.

13. Elaine, A., Lourdes, F., Alfonso, R. and Jordi, P. (2002). Study on the degradability of Poly (ester amide)s related to nylons and polyesters 6, 10 or 12,10. *Macromolecular Chemistry and Physics;* 203, 48-58.

14. Phares, K., Cho, M., Johnson, K. and Swarbrick, J. (2002). Drug transport across nylon 6,10 films: Influence of synthesis variables. *Pharmaceutical Research;* 12, 248-256.

15. Madan, P. L. and Chareonboonsit, P. (1989). Nylon microcapsules. II. Effects of selected variables on theophylline release. *Pharmaceutical Research;* 6, 714-718.

16. Koulouri, E. G., Scourlis, E. G. and Kallitsis, J. K. (1999). Characterization of melt-mixed blends of poly (ether-ester) with various polyamides. *Polymer,* 40, 4887-4896.

17. Koulouri, E. G., Georgaki, A. X. and Kallitsis, J. K. (1997). Reactive compatibilization of aliphatic polyamides with functionalized polyethylenes. *Polymer,* 38: 4185-4192.

18. Chattaraj, S. C., Swarbrick, J. and Kanfer, I. (1995). A simple diffusion cell to monitor drug release from a semisolid dosage form. *International Journal of Pharmaceutics,* 120, 119-129.

19. Escander, G. M., Gonzalez Gomez, D., Espinosa Mansilla, A., Munoz de la Pena, A. and Goicoechea H. C. (2004). Determination of carbamazepine in serum and pharmaceutical preparations using immobilization on a nylon support and fluorescence detection. *Analytica Chimica Acta,* 506, 161-170.

20. Bugg, M., Bradly, G. and Sullivan, A. (2004). Polymer-filler interactions in kaolin/nylon6,6 composites containing a silane coupling agent. *Composites Part A: Applied Science and Manufacturing,* 36, 437-442.

21. Gaymans, R. J. and Sikkema, D. J. in 'Aliphatic Polyamides', ed. Allen, S. G., Beoington, C. B. and Price, C., *Comprehensive Polymer Science,* 1999 vol. 5, p. 357-373.

22. Saartrat, S., Puttanlek, C., Rungsardthong, V. and Uttapap, D. (2005). Paste and gel properties of low-substituted acetylated canna starches. *Carbon Polymer,* 61, 211-221.

23. El-Sherbiny, I. M., Lins, R. J., Abdel-Bary, E. M. and Harding, D. R. K. (2005). Preparation, characterization, swelling and in-vitro drug release behavior of poly [N-acryloylglycine-chitosan] inter-polymeric pH and thermally-responsive hydrogels. *European Polymer Journal;* 41: 2584-2591.

24. Sibanda, W., Pillay, S., Danckwerts, M. P., Viljoen, A. M., Vuuren, S. and Khan, R. A. (2004). Experimental design for the formulation and optimization of novel cross-linked oilispheres developed for in vitro site-specific release of Mentha piperita oil. *AAPS Pharmaceutical Science and Technology,* 5: 1-14.

25. Pillay, V. and Fassihi, R. (1999). In vitro release modulation of cross-linked pellets for site-specific drug delivery to the gastrointestinal tract, II. Physicochemical characterization of calcium-alginate, calcium-pectinate and calcium-alginate-pectinate pellets. *Journal of Controlled Release;* 59: 243-256.

26. Johnson, F. A., Craig, D. Q. M., Mercer, A. D and Chauhan, S. (1997). The effects of alginate molecular structure and formulation variables on the physical characteristics of alginate raft systems. *International Journal of Pharmaceutics;* 159, 35-42.

27. Jones, D. S., Woolfson, A. D. and Brown, A. F. (1997). Textural, viscoelastic and mucoadhesive properties of pharmaceutical gels composed of cellulose polymers. *International Journal of Pharmaceutics;* 151, 223-233.

28. Pillay, V. and Danckwerts, M. P. (2002). Textural profiling and statistical optimization of crosslinked calcium-alginate-pectinate-cellulose acetophthalate gelisphere matrices. *Journal of Pharmaceutical Science;* 91: 2559-2570.

29. Pillay, V. and Fassihi, R. (1999). In vitro release modulation of cross-linked pellets for site-specific drug delivery to the gastrointestinal tract, II. Physicochemical characterization of calcium-alginate, calcium-pectinate and calcium-alginate-pectinate pellets. *Journal of Controlled Release;* 59: 243-256.

30. Kuentz M. and Rothlisberger D. (2002). Determination of the optimal amount of water in liquid-fill masses for hard gelatin capsules by means of textural analysis and experimental design. *International Journal of Pharmaceutics,* 236, 145-152.

31. Plackett R. L. and Burman J. P. (1946). The design of optimum multifactorial experiments. *Biometrika,* 33, 305-325.

32. Sastry S. V. and Khan M. A. (1998). Aqueous based polymeric dispersion: Plackett-Burman design for screening of formulation variables of atenolol gastrointestinal therapeutic system. *Pharmaceutica Acta Helvetiae,* 73, 105-112.

33. Abdel-Fattah Y. R., Saeed H. M., Gohar Y. M. and El-Baz M. A. (2005). Improved production of *Pseudomonas aeruginosa* uricase by optimization of process parameters through statistical experimental design. *Process Biochemistry,* 40, 1707-1714.

34. Kincl M., Turk S. and Vrecer F. (2005). Application of experimental design methodology in development and optimization of drug release method. *International Journal of Pharmaceutics,* 291, 39-49.

35. Nutan M. T. H., Soliman M. S., Taha E. I. and Khan M. A. (2005). Optimization and characterization of controlled release multi-particulate beads with starch acetate. *International Journal of Pharmaceutics,* 294, 89-101.

36. Jones D. S., Woolfson, D. A., Djokic J. and Coulter W. A. (1996). Development and mechanical characterization of bioadhesive semi-solid, polymeric systems containing tetracycline for the treatment of periodontal diseases. *Pharmaceutical Research,* 13, 1734-1738.

37 Ghosh, S. (2004). Recent research and development in synthetic polymer-based drug delivery systems. *J. Chem. Res.;* 4: 241-246.

38. Gaymans, R. J. and Sikkema, D. J. (1999). In "Aliphatic polyamides", ed. Allen, S. G., Beoington, C. B. and Price, C. in *Comprehensive Polymer Science, Vol.* 5, pgs 357-373.

39. Lundborg G., Dahlin L., Dohi D., Kanje M. and Terada N. (1997). A new type of "bioartificial" nerve graft for bridging extended defects in nerves. *J. Hand Surgery (British and European Volume)* 22B: 299-303.

40. Dolorico A. M. T., Ramin T., Hung V. O. and Ronald N. G. (2003). Short-term and long-term visual and astigmatic results of an opposing 10-0 nylon double running suture technique for penetrating keratoplasty. *Journal of the American College of Surgery;* 197: 991-999

41. Seitz B., Langenbucher A., Küchle M. and Naumann G. O. H. (2003). Impact of graft diameter on corneal power and the regularity of postkeratoplasty astigmatism before and after suture removal. *Opthalmology*, 110: 2162-2167.

The invention claimed is:

1. A polyamide rate-modulated monolithic drug delivery system comprising at least one active compound and a biodegradable and biocompatible synthetic aliphatic polyamide polymer selected for delivering the active compound within a predetermined time frame to a target organism.

2. The polyamide rate-modulated monolithic drug delivery system of claim 1, wherein the active compound is a pharmaceutical compound for application to humans or animals.

3. The polyamide rate-modulated monolithic drug delivery system of claim 1, wherein the active compound is a biocidal composition for use in controlling animal and/or plant pests.

4. The polyamide rate-modulated monolithic drug delivery system of claim 1, wherein the polymer is modified by salting-out or crosslinking the polymeric material to achieve the desired biodegradability characteristics and to control the release of the active compound.

5. The polyamide rate-modulated monolithic drug delivery system of claim 2, wherein the polymer and active compound are present in a dosage form suitable for oral administration.

6. The polyamide rate-modulated monolithic drug delivery system of claim 5, wherein the dosage form is a tablet.

7. The polyamide rate-modulated monolithic drug delivery system of claim 2, wherein the polymer and active compound are present in a dosage form suitable for implantation in a human or animal body.

8. The polyamide rate-modulated monolithic drug delivery system of claim 3, wherein the polymer and active compound are present in a dosage form suitable for application by spraying.

9. The polyamide rate-modulated monolithic drug delivery system of claim 3, wherein the polymer and active compound are present in a dosage form suitable for application by dusting.

10. The polyamide rate-modulated monolithic drug delivery system of claim 3, wherein the polymer and active compound are in the form of a flowable powder.

11. The polyamide rate-modulated monolithic drug delivery system of claim 1, wherein the polymer and the active compound form a matrix which biodegrades at a predetermined rate to release the active compound over a predetermined period of time.

12. The polyamide rate-modulated monolithic drug delivery system of claim 11, wherein a metal hydroxide is added to the matrix to reinforce the matrix integrity and to limit outward diffusion of the active compound.

13. The polyamide rate-modulated monolithic drug delivery system of claim 12, wherein the metal hydroxide is sodium hydroxide.

14. The polyamide rate-modulated monolithic drug delivery system of claim 11, wherein an organic solvent is added to the matrix to reinforce the matrix integrity and to limit outward diffusion of the active compound.

15. The polyamide rate-modulated monolithic drug delivery system of claim 14, wherein the organic solvent is cyclohexane.

16. The polyamide rate-modulated monolithic drug delivery system of claim 1, wherein the synthetic aliphatic polyamide is a 6,10 variant thereof.

17. The polyamide rate-modulated monolithic drug delivery system of claim 1, wherein the physicochemical and physicomechanical properties of the polymer are enhanced by optimizing the stoichiometry of a monomer composition, solvent phase modifiers and/or conditions of polymeric synthesis.

18. The polyamide rate-modulated monolithic drug delivery system of claim 17, wherein the physicochemical and physicomechanical properties of the polymer are enhanced by optimizing its molecular mass, crystallinity, porosity, melting temperature, solubility, matrix resilience, matrix hardness and deformation energy or combination thereof.

19. The rate-modulated monolithic drug delivery system of claim 16, wherein the polymer is enhanced by a modified interfacial polymerization approach in order to optimize the release of an active compound in terms of the order and release rate.

20. The rate-modulated monolithic drug delivery system of claim 19, wherein the synthetic aliphatic polyamide 6,10 variant has had its physicochemical and physicomechanical properties optimized as a result of modifying the stoichiometry of monomer composition, solvent phase modifiers and the conditions of polymeric synthesis.

21. The rate-modulated monolithic drug delivery system of claim 20, wherein the physicochemical and physicomechanical properties of the polyamide have been optimized by altering one or more of its molecular mass, crystallinity, porosity, melting temperature, solubility, matrix resilience, matrix hardness and deformation energy.

22. The rate-modulated monolithic drug delivery system of claim 16, wherein solvent phase modifiers are added to the polymer to alter the solvent pH and polarity to enhance the matrix integrity of the rate-modulated monolithic drug delivery system, and also influencing the polymeric diffusivity.

23. The rate-modulated monolithic drug delivery system of claim 22, wherein the solvent phase modifier is a metal hydroxide.

24. The rate-modulated monolithic drug delivery system of claim 23, wherein the metal hydroxide is sodium hydroxide.

25. The rate-modulated monolithic drug delivery system of claim 22, wherein the solvent phase modifier is an organic solvent.

26. The rate-modulated monolithic drug delivery system of claim 25, wherein the organic solvent is cyclohexane.

* * * * *